United States Patent [19]
Langley et al.

[11] Patent Number: 5,611,997
[45] Date of Patent: Mar. 18, 1997

[54] APPARATUS FOR PRODUCING BLOOD COMPONENT PRODUCTS

[75] Inventors: Robert W. Langley, Westminister; Larry J. Dumont, Arvada, both of Colo.

[73] Assignee: COBE Laboratories, Inc., Lakewood, Colo.

[21] Appl. No.: 457,840

[22] Filed: Jun. 1, 1995

Related U.S. Application Data

[63] Continuation of Ser. No. 912,973, Jul. 10, 1992.

[51] Int. Cl.⁶ .......................... G01N 33/00; G06F 15/00
[52] U.S. Cl. ........................ 422/73; 422/72; 436/10; 436/63; 436/69; 436/70; 436/174; 436/177; 435/2
[58] Field of Search ..................... 436/10, 63, 69, 436/70, 174, 175, 177, 45; 435/2; 422/72, 73; 356/39; 128/DIG. 13; 364/413.01, 413.07, 413.08, 413.09; 604/4, 5, 6

[56] References Cited

U.S. PATENT DOCUMENTS

| | | | |
|---|---|---|---|
| 4,094,461 | 6/1978 | Kellogg et al. | 233/40 |
| 4,459,997 | 7/1984 | Sarstedt | 128/764 |
| 4,657,529 | 4/1987 | Prince et al. | 604/6 |
| 4,810,090 | 3/1989 | Boucher et al. | 356/39 |
| 4,851,126 | 7/1989 | Schoendorfer | 210/651 |
| 4,968,295 | 11/1990 | Neumann | 604/6 |
| 4,976,271 | 12/1990 | Blair | 128/764 |
| 5,096,573 | 3/1992 | Bermudez | 210/85 |
| 5,153,828 | 10/1992 | Inoue et al. | 364/413.07 |
| 5,178,603 | 1/1993 | Prince | 604/6 |
| 5,437,624 | 8/1995 | Langley | 604/4 |
| 5,496,265 | 3/1996 | Langley et al. | 604/5 |

FOREIGN PATENT DOCUMENTS

WO84/00112  1/1984  WIPO.

OTHER PUBLICATIONS

Cobe Spectra™ Apheresis System, Operator's Manual, (Sections 1, 3A, 3B, 4A, 4B and Appendix B) (Approved for Publication Feb. 12 1991).

*Primary Examiner*—Jill Warden
*Assistant Examiner*—Maureen M. Wallenhorst
*Attorney, Agent, or Firm*—Sheridan Ross P.C.

[57] ABSTRACT

An apparatus for producing blood component products. In one embodiment, a plurality of a predetermined type of blood component is harvested from a source of whole blood. At least two on-line yield determination techniques are utilized to determine the yield of the harvested blood components. One is a predetermined yield prediction technique and the second is a predetermined yield monitoring technique, each of which are individually calibrated in relation to a predetermined off-line yield determination technique. The predetermined yield prediction and monitoring techniques each provide the yield of the harvested blood components and each is then utilized to provide a determined yield. Consequently, when the harvested blood components are packaged the determined yield may be associated therewith, thereby providing a blood component product.

10 Claims, 7 Drawing Sheets

\*_____ associated with blood/blood components
\*------ associated with information/data

APPARATUS FOR PRODUCING BLOOD COMPONENT PRODUCTS

RELATED APPLICATIONS

This application is a continuation of pending U.S. patent application Ser. No. 07/912,973, filed Jul. 10, 1992, and entitled "METHOD AND APPARATUS FOR PRODUCING BLOOD COMPONENT PRODUCTS".

FIELD OF THE INVENTION

The present invention generally relates to blood component harvesting and, more particularly, in one application to a method and apparatus for producing platelet products, namely a collection of harvested platelets having a determined yield associated therewith.

BACKGROUND OF THE INVENTION

The utilization of blood taken from donors and infused into recipients is well known for purposes of treating medical emergencies and other conditions. More recently, selected blood components have been harvested from blood for subsequent infusion into recipients requiring blood component therapy. As used herein, "harvesting" means the separation/removal of a particular type of blood component from remaining portions of the whole blood.

In order to harvest blood components, blood is removed from a donor by a needle assembly or other blood access device and is thereafter processed utilizing centrifugation or other appropriate separation techniques to isolate and collect the desired components. This procedure is carried out most effectively in an on-line, continuous process wherein blood is removed from a donor, processed through a disposable extracorporeal circuit to obtain the desired components, and returned to the donor. Once the harvested blood components are collected in this manner, it is often necessary to subject such components to an "off-line yield determination technique." As used herein, "off-line yield determination technique" means any laboratory analysis performed in accordance with a predetermined laboratory testing regime (i.e., utilizing a particular blood component counting technique with a specific predetermined apparatus and protocol). For instance, in the case of harvested platelets laboratory testing is required (e.g., governmental/industry regulations/standards) or otherwise desired to identify platelet yield prior to distribution. More particularly, under some circumstances associating a platelet yield (e.g., the number of platelets in a harvested collection or any other value from which such may be derived) within a particular collection of platelets may be integral in the provision of such as a platelet product.

Laboratory testing of blood components typically entails the use of expensive equipment and relatively time-consuming procedures, and therefore the use of off-line yield determination techniques is not feasible for many blood harvesting facilities. Consequently, these facilities are forced to ship their collections of harvested blood components to off-site, third-party laboratories meeting the relevant requirements. As can be appreciated, such third-party laboratory testing of harvested blood components adds significant cost and delay in the provision of blood component products.

In the latter regard, certain "on-line yield determination techniques" have been developed to assist blood component harvesting facilities in donor yield/schedule planning and donor-specific harvesting procedures. As used herein, "on-line yield determination technique" means any technique, other than off-line yield determination techniques (i.e., actual laboratory testing), to forecast the yield of harvested/collected blood components. Of particular interest, a platelet yield prediction technique has been developed which is based upon donor-specific physical data (e.g., donor blood volume, hematocrit, and platelet precount) and harvest procedure-specific information (e.g., needle information, device collection efficiency, volume of concurrent source plasma collection, whole blood and anticoagulant flow rates, anticoagulant infusion rate, and procedure duration). Relatedly, harvesting/collection monitoring techniques have been employed in which, for example, optical measurements are taken during platelet collection to determine platelet concentration from which platelet yield is determined. By way of example, each of the noted prediction and monitoring techniques are incorporated in the COBE Spectra™, a product of Cobe BCT, Incorporated, 1201 Oak Street, Lakewood, Colo. 80215.

While such prediction and monitoring techniques have proven to be useful for planning purposes, experience reflects discrepancies between yield values generated thereby and the corresponding yield values obtained by off-line yield determination techniques. Moreover, it is generally believed that there is a laboratory-to-laboratory variance in determining yields, even when employing similar off-line yield determination techniques.

SUMMARY OF THE INVENTION

The present invention is directed to a method and apparatus for producing blood component products, namely a collection of harvested blood components having a determined yield associated therewith. The invention is based in part upon a recognition that variability in off-line yield determination techniques, utilizing for instance predetermined laboratory counting equipment and procedures, should be accounted for in determining the blood component product yield by on-line yield determination techniques.

In one aspect, the present invention is a method for providing a desired blood component product, namely a collection of a plurality of a desired blood component having a determined yield, in relation to a predetermined off-line yield determination technique. The method comprises two general steps: obtaining a collection of desired blood components and determining the yield of such blood components by at least one on-line yield determination technique. More particularly, a desired blood component (e.g., platelets) is harvested from a source of whole blood (e.g., a donor) in an appropriate manner (e.g., centrifugation). A first calibration factor is established for the at least one predetermined on-line yield determination technique, more particularly a predetermined yield prediction technique, in relation to the predetermined off-line yield determination technique. As it is employed herein, the term "predetermined yield prediction technique" means any technique, not involving measurements conducted on the harvested blood components, that may be employed to predict blood component yield for a given blood component harvesting operation. The predetermined yield prediction technique is utilized to obtain a first predicted yield value for the harvesting operation, and the first calibration factor is thereafter applied to the first predicted yield value to obtain a second predicted yield value. The determined yield for the collected blood components is thereafter derived at least in part from this second predicted yield value. Consequently, when the collected blood components are packaged, the determined yield may be associated therewith by recording the yield in some manner (e.g., by indicating the yield directly on the packaging, or by inputting the yield into a data base with a corresponding identifier which is also indicated on the packaging), such that a blood component product is provided.

The method of the above-identified aspect of the present invention may further comprise the step of monitoring the harvested blood components during at least a portion of the harvesting step to obtain a first monitored yield value, namely by utilizing another on-line yield determination technique in the nature of a predetermined yield monitoring technique. As employed herein, the term "predetermined yield monitoring technique" means any technique, involving measurements conducted in conjunction with a harvesting operation on harvested blood components, that may be employed to monitor blood component yield for the blood component harvesting operation. A second calibration factor may then be established for the predetermined yield monitoring technique in relation to the predetermined off-line yield determination technique. Once this second calibration factor is established, it may be applied to the first monitored yield value to obtain a second monitored yield value. In order to enhance accuracy, the determined yield may then be derived from both the second predicted yield value and the second monitored yield value.

In addition to increasing the potential for achieving an accurate determined yield by utilizing both the second predicted yield value and the second monitored yield value, generating both such yield values allows for an assessment of the likelihood that a determined yield value will fall within an acceptable range of accuracy, thereby enhancing quality control. More particularly, if in appropriately comparing the second predicted yield value and second monitored yield value a determination is made that the difference therebetween is outside a certain predefined statistical parameter, the collection of blood components can be sent to a laboratory for a determination of yield by, for instance, the predetermined off-line yield determination technique.

The first and/or second calibration factors utilized in the method of the above-identified aspect may each be established by conducting a blood component harvesting operation for at least one, and preferably for a plurality of first blood sources to obtain an associated first blood component sample(s). The predetermined yield prediction technique may thus be employed for each of such first blood component samples to obtain an associated first predicted yield value, and/or the predetermined yield monitoring technique may be utilized for each of such samples to obtain an associated first monitored yield value. Each of the first blood component samples may also be subjected to the predetermined off-line yield determination technique to obtain corresponding off-line measured yield values for such samples.

Having obtained the foregoing yield values, an initializing first calibration factor may be obtained for each of the first blood component samples by dividing the off-line measured yield value by the associated first predicted yield value for each such sample. The mean of these initializing first calibration factors may then taken to establish the first calibration factor. Similarly, an initializing second calibration factor may be obtained for each of the first blood component samples by dividing the off-line measured yield value by the associated first monitored yield value. The mean of these initializing second calibration factors may then be taken to establish the second calibration factor. As can be appreciated, the size of the calibration group (e.g., first blood sources) will of course determine in part the statistical significance of the respective first and second calibration factors.

In the event that the first and second calibration factors are obtained in the above-described manner, the related information may be utilized by the present invention by further potential steps to ensure that such calibration factors are properly maintained. For instance, at least one, and preferably a plurality of second blood sources may be subjected to an appropriate separation procedure to obtain an associated second blood component sample(s). The yield for each of these second blood component samples may be obtained by each of the predetermined yield prediction technique, the predetermined yield monitoring technique, and the predetermined off-line yield determination technique. A test first calibration factor may be obtained for each of the second blood component samples by dividing the off-line measured yield value by the first predicted yield value. Similarly, a test second calibration factor for each of the second blood component samples may be obtained by dividing the off-line measured yield value by the first monitored yield value. The mean may be taken of the plurality of first test calibration factors, and a mean may be taken for the plurality of test second calibration factors. Moreover, a mean may be taken of the combination of the initializing first calibration factors and the test first calibration factors, and similarly for the combination of the initializing second calibration factors and the test second calibration factors. The mean of the test first calibration factors and/or the mean of the combination of initializing/test first calibration factors may be utilized to verify the suitability of the first calibration factor, and similarly the mean of the test second calibration factors and/or the mean of the combination of initializing/test second calibration factors may be utilized to verify the suitability of the second calibration factor.

In another aspect, the present invention is a system for providing a blood component product, namely a collection of harvested blood components having a determined yield provided in accordance with at least one on-line yield determination technique. The system generally entails the harvesting of such blood components, the provision of predetermined information, and the use of such information to obtain the yield of harvested blood components by such on-line yield determination technique(s) to provide the desired blood component product.

More particularly, the system includes a means for harvesting the blood components from a source of blood. As a result, a plurality of blood components are collected for distribution as a blood component product after determining the yield thereof in accordance with the present invention. The yield of the harvested blood components is based, in part, upon certain categories of information provided by an operator of the system to appropriate portions thereof. More particularly, a system component (e.g., keyboard and microprocessor) is provided for inputting/receiving: a first set of information relating to the source of the blood (e.g., donor weight, height); and a second set of information relating to the means for harvesting (e.g., collection efficiency, single or dual needle configuration). Based upon this operator-input information, a system component (e.g., microprocessor) generates a first predicted yield value.

The system further includes a system component(s) for providing a first calibration factor, based upon the system component(s) which generates the predicted yield value in relation to a predetermined off-line yield determination technique. This predetermined off-line yield determination technique allows/provides for an off-line measured yield value for the harvested blood components. For instance, the off-line measured yield value and predicted yield value for a plurality of runs on the system may be utilized to statistically generate the first calibration factor. Based upon this information, a system component(s) generates the determined yield at least in part by the application of the first calibration factor to the predicted yield value. Consequently, the harvested blood components may be packaged and the determined yield associated therewith to provide the desired blood component product.

In order to further enhance the potential for a desired degree of accuracy for the determined yield, the above-identified system may further include a system component(s) for providing another on-line yield determination technique, namely to provide a monitored yield value for the harvested blood components based upon a monitoring of the harvested blood components. Consequently, a system component(s) may provide a second calibration factor based upon the system component(s) which provides the monitored yield value in relation to the predetermined off-line yield determination technique. In this case, the system component(s) which generates the determined yield may thus utilize both the application of the first calibration factor to the predicted yield value, as well as the application of the second calibration factor to the monitored yield value, to obtain the determined yield.

In another aspect, the present invention is an assembly for providing a blood component product, namely a collection of harvested blood components having a determined yield pursuant to at least two on-line yield determination techniques. More particularly, a means is provided for harvesting (e.g., a centrifuge) the desired blood components (e.g., platelets) from the source of blood. Furthermore, means are provided for providing a first predicted yield value of the harvested blood components and means are also provided for monitoring the harvested blood components to obtain a first monitored yield value. A first calibration factor is applied to the first predicted yield value and a second calibration factor is applied to the first monitored yield value to obtain a second predicted yield value and second monitored yield value, respectively. The first and second calibration factors are based upon the means for providing the first predicted yield value and the means for monitoring, respectively, both in relation to a predetermined off-line yield determination technique. The determined yield is then derived from the second predicted yield value and the second monitored yield value such that when the collected blood components are packaged, a blood component product may be provided, namely one having a determined blood component yield with a specified confidence level or probability of not being less than the yield as would be measured by the predetermined off-line yield determination technique (e.g., laboratory equipment/protocol).

The method and apparatus of the present invention have particular applicability to platelet harvesting operations. In particular, it is believed that platelet products produced in accordance with the present invention largely reduce the need for subjecting harvested platelet products to subsequent laboratory testing before distribution.

DETAILED DESCRIPTION

Figure 1:
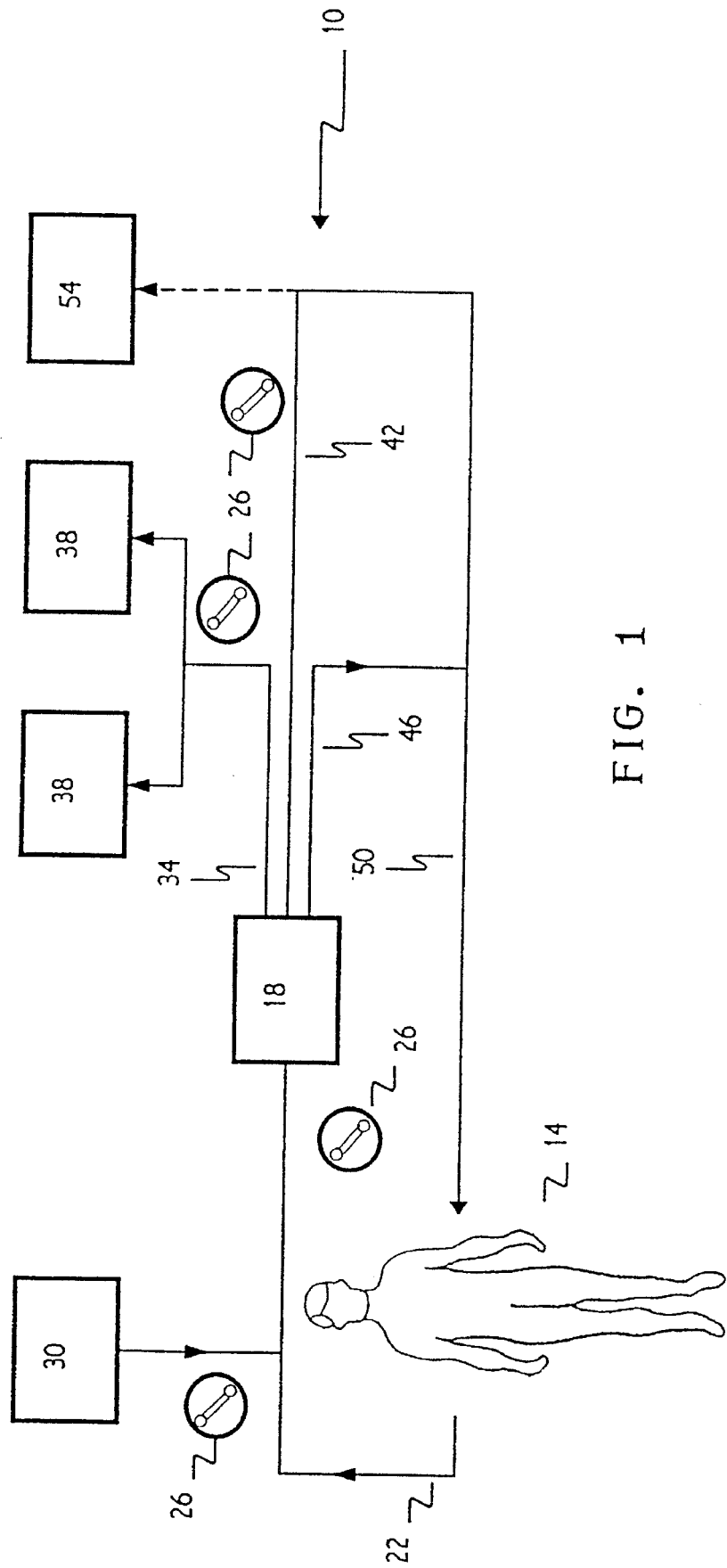
FIG. 1 is a schematic representation of one embodiment of a blood component separation assembly which utilizes a dual needle configuration.

The present invention will be described with reference to the accompanying drawings which assist in illustrating the pertinent features thereof. In this regard, the present invention is generally a method and apparatus for producing blood component products. These blood component products have a known and associated blood component yield, determined by a desired manner pursuant to the present invention in at least one on-line yield determination technique, for purposes of providing desired information and/or determining compliance with governmental/industry regulations/standards. Although the principles of the present invention may be applicable to a variety of applications, in one embodiment the desired blood components are platelets which are harvested from whole blood provided by a donor.

Generally, the present invention combines two primary aspects. One is the actual harvesting of a predetermined type of blood component from a source of whole blood. The other is the determination of the yield of the harvested blood components in a particularly desirable manner, namely using at least one on-line yield determination technique, and the subsequent association of the determined yield with the harvested blood components to provide the blood component product. As will be discussed in more detail below, this yield determination can be provided without submission of the harvested blood components to a laboratory for yield determination utilizing an off-line yield determination technique as previously standard procedure.

As noted above, one application of the present invention is the harvesting of platelets from whole blood provided by a donor. Consequently, for exemplary purposes the principles of the present invention will be described with regard to this specific application. However, those skilled in the art will appreciate that such principles may be extended to a variety of other applications for removal of blood components therefrom, all of which are within the scope of the present invention to the extent permitted by the prior art.

The initial aspect of the present invention utilizes the principles of centrifugation or other appropriate techniques to separate and harvest the predetermined type of blood component from the source of whole blood. In one embodiment, the harvesting of the desired platelets may be performed in an on-line procedure as illustrated by the blood component separation assembly 10 of FIG. 1. This particular configuration is commonly referred to as a dual needle configuration since there are two fluid interconnections between a given donor 14 (e.g., blood supply) and a centrifuge 18 (e.g., blood component separation apparatus) which is utilized to separate and harvest the platelets from the donor's 14 blood. In this regard, the donor 14 is fluidly connected to the centrifuge 18 via a centrifuge inlet line 22 and appropriate needle assembly (not shown). Whole blood from the donor 14 is thus continuously provided to the centrifuge 18 through the centrifuge inlet line 22 for separation of the platelets therefrom, utilizing a peristaltic pump 26 to maintain this flow if desired/required. Prior to the donor's 14 blood entry into the centrifuge 18, anticoagulant from an anticoagulant ("AC") container 30 may be provided to the whole blood, again utilizing a peristaltic pump 26 to maintain this particular flow if desired/required.

The centrifuge 18 separates the whole blood provided on-line by the donor 14 into three primary constituents, namely platelets, red blood cells ("RBC"), and plasma. The platelets collected from the centrifuge 18 are directed through a platelet collect line(s) 34 to one or more platelet collect bags 38 via a peristaltic pump 26. The plasma and RBCs are provided back to the donor 14 through a plasma line 42 and RBC line 46, respectively, both of which are interconnected with a second needle assembly (not shown) on the donor 14 via a donor return line 50. Alternatively, it may be desirable to collect the separated plasma. In this regard, a plasma collect bag 54 may be provided and interconnected with the plasma line 42 (interconnection shown in phantom).

Notwithstanding the advantages associated with the continuous, on-line, dual needle harvesting capabilities of the blood component separation assembly 10 of FIG. 1, those skilled in the art will appreciate that the source of blood may be provided to the centrifuge 18 from an appropriate blood container (not shown) interconnected with the centrifuge 18, versus receiving such directly from the donor 14. Moreover, the blood of course may be provided from alternative sources such as animals. Furthermore, as illustrated in FIG. 2 this platelet harvesting procedure may be performed utilizing a single needle configuration.

Figure 2:
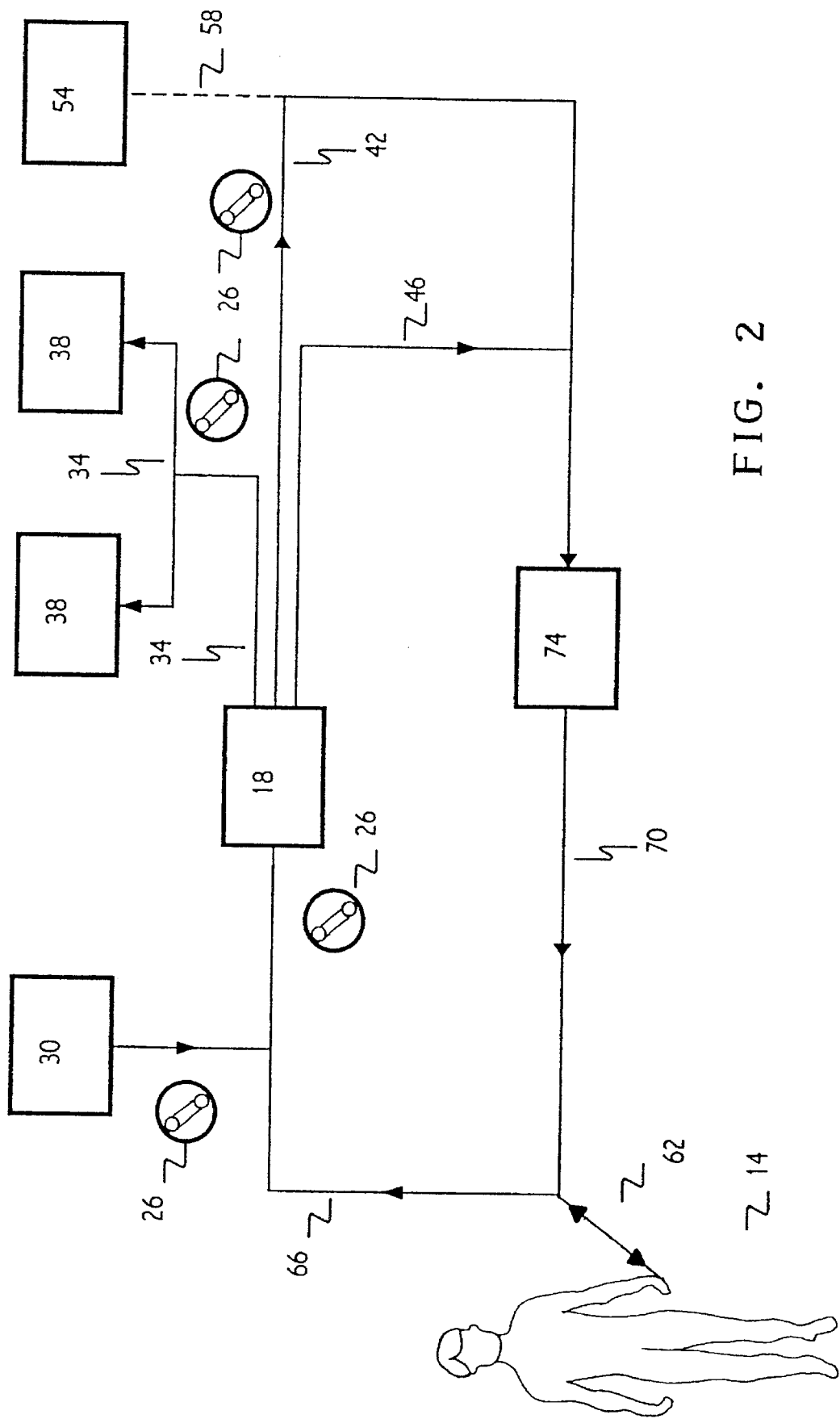
FIG. 2 is a schematic representation of one embodiment of a blood component separation assembly which utilizes a single needle configuration.

The blood component separation assembly 58 of FIG. 2 is similar to that of the dual needle configuration of FIG. 1 except that a single needle assembly (not shown) incorporates the donor 14 within the blood component separation assembly 58. Consequently, similar components are similarly identified. With regard to the single needle configuration of FIG. 2, the whole blood of the donor 14 initially flows through a donor access line 62 and into a centrifuge inlet line 66 which is fluidly connected with the centrifuge 18 such that the platelets are harvested in the above-described manner. The plasma and RBC from the centrifuge 18 flow through the plasma and RBC lines 42, 46, respectively, both of which are fluidly interconnected with a return flow controller 74. As above, however, the plasma may alternatively be directed to a plasma collect bag 54. In the event that plasma is not collected, the RBC and plasma are provided back to the donor 14 through the return flow controller 74 via a donor return line 70 which is interconnected with the donor access line 62. As can be appreciated, since only a single line is directly connected to the donor 14, namely the donor access line 62, blood is either being removed from or provided to the donor 14 such that the procedure is effectively two-step versus continuous.

One embodiment of a centrifuge 18 is the subject of U.S. Pat. No. 4,094,461 to Kellog et al., entitled "CENTRIFUGE COLLECTING CHAMBER" issued Jun. 13, 1978, and incorporated by reference in its entirety herein. This centrifuge 18 is also commercially available from the assignee of the present application as such is incorporated in the COBE Spectra™. Generally, this type of centrifuge includes a disposable assembly which is positionable and retained within a centrifuge bowl. The disposable assembly includes an annular separation channel and a collection chamber which is positioned between the inlet and outlet to the channel. Blood is provided to the inlet of the annular separation chamber during rotation of the centrifuge bowl and is thus separated into the various fractions by centrifugal force. Such fractions include RBC, platelets, and plasma in order of decreasing density.

The separated platelet-poor plasma and concentrated platelet fractions flow from the separation chamber into the collecting chamber. The collecting chamber is separated from the separation chamber by a dam. The concentrated platelets collect in the collecting chamber such that this fraction may be removed and collected in a bag. The plasma and RBC are also removed from the separation chamber and provided back to the donor 14 (FIGS. 1–2) and/or collected as required/desired.

Notwithstanding of the description of the particular centrifuge associated with U.S. Pat. No. 4,094,461, those skilled in the art will appreciate that a variety of other configurations of centrifuges may be utilized to harvest platelets in the manner provided by the blood component separation assemblies 10, 58. Moreover, those skilled in the art will also appreciate that alternative apparatus/methods may be used to harvest blood components. Furthermore, those skilled in the art will appreciate that other configurations of blood component separation assemblies may be similarly utilized.

Once the platelets are collected by centrifugation in the illustrated procedures of FIGS. 1 or 2, the yield of such platelets must typically be associated therewith for provision of the defined platelet product, thereby combining the harvesting and yield determination aspects to provide the present invention. As noted above, the present invention allows for this yield determination without requiring submission of such harvested blood components to a laboratory for the performance of an off-line yield determination technique thereon as standard procedure.

Generally, the yield determination aspect to provide the combination required by the present invention is provided in one embodiment by a predetermined yield prediction technique and a predetermined yield monitoring technique. The yields provided by these techniques are each adjusted by a calibration factor specific to each of such techniques in relation to a predetermined off-line yield determination technique which would be otherwise utilized as a matter of course to analyze the platelets to obtain an off-line measured yield value.

A predetermined yield prediction technique is utilized in the derivation of the yield to be associated with the harvested platelets to thereby provide the defined platelet product. Although a variety of predetermined yield prediction techniques may be suitable for purposes of combining with the above-described harvesting aspect to provide the present invention, in one embodiment the predetermined yield prediction technique generates a predicted yield value based upon a variety of categories of information/generated data such as the blood supply (e.g., donor 14) and the particulars of the harvesting protocol (e.g., collection efficiency).

In the identified embodiment, the predetermined yield prediction technique considers parameters such as whether the platelet production procedure is single or dual needle; whether concurrent source plasma is collected; the total blood volume of the donor; donor hematocrit; donor platelet precount; anticoagulant ratio; anticoagulant infusion rate constant; procedure time; and platelet concentration of the collected platelets. Further, the predetermined yield prediction technique utilizes a calibration factor. Generally, the yield prediction calibration factor relates the predetermined yield prediction technique to a predetermined off-line yield determination technique which could be employed to obtain an off-line measured yield value.

The above-identified types of parameters are generally utilized by the predetermined yield prediction technique as follows: (1) the anticoagulant ratio, donor hematocrit, inlet flow rate, and needle number option are used to determine the collection efficiency for a given procedure; (2) the AC infusion rate constant, AC ratio, volume of platelet product collected, volume of source plasma collected, inlet flow rate, and procedure time are utilized to determine the volume of whole blood processed; and 3) donor blood volume, donor platelet precount, volume of whole blood processed, collection efficiency, and yield calibration factor are utilized to determine the predicted platelet yield.

In one embodiment, the general form of the predetermined yield prediction technique is provided by the following equation:

$$Y = 1 \times 10^6 \, C_{PR} V_B F_Y [1 - exp[-E_C(f_{BP} - f_I)]] \quad \text{(Equation 1)}$$

where $Y$ = platelet yield, number of platelets $C_{PR}$ = donor precount, $10^3$ platelets/microliter $V_B$ = total blood volume of donor, ml $F_Y$ = yield calibration factor $E_C$ = platelet collection efficiency $f_{BP}$ = fraction of $V_B$ processed in the procedure $f_I$ = fraction of $V_B$ required by blood component separation device before platelet collection begins.

$C_{PR}$ and $V_B$ define the size of the initial platelet pool being processed, and the first-order exponential decay accounts for the depletion of the platelet pool in the course of the procedure. If the blood pool is not recirculated during the procedure, Equation 1 becomes linear.

$E_C$ is specific to each type of blood component separation device, and depending upon the type of device, whether centrifugal, filter, or other means, can be a function of process variables like the number of needles (i.e., whether a batch or continuous process is utilized) and the rate of which whole blood is processed.

The magnitude of $f_{BP}$ depends on the specifics of the procedural protocol such as the rate at which whole blood is drawn from the donor and the procedure time. The magnitude of $f_I$ depends on the specifics of the device and the procedural protocol, such as type of device, size of separation volume, blood flow rate, and flow patterns within the separation volume.

The solution to Equation 1 may be complex and iterative, depending upon the interrelationships between $E_C$, $f_{BP}$ and $f_I$, as expressed in terms of other procedural variables such as flow rate, centrifuge speed, number of needles, etc. However, all the above variables are knowledge readily available to the manufacturer of any blood component separation device.

$F_Y$ is the yield calibration factor that has been previously discussed. Its function is to remove the average discrepancy that may exist between the yield as predicted by Equation 1 and the yield as provided by the associated predetermined off-line yield determination technique.

An on-line platelet yield monitoring technique may also be incorporated by the present invention to derive the yield to be associated with a given collection of harvested platelets so as to provide a platelet product. During the harvesting of platelets by centrifugation in the above-described manner, or by some other means, the concentration of the platelets collected from the centrifuge 18 may be determined by incorporating an on-line monitoring device. One such device is disclosed in U.S. Pat. No. 4,810,090 to Boucher et al., entitled "METHOD AND APPARATUS FOR MONITORING BLOOD COMPONENTS," and issued Mar. 7, 1989. U.S. Pat. No. 4,810,090 is incorporated by reference in its entirety herein.

Generally, the on-line monitoring of platelet concentration disclosed by U.S. Pat. No. 4,810,090 is referred to as a Collect Concentration Monitor ("CCM") and utilizes an optical detector system (not shown herein) in which light is directed through the flow of platelets collected from the centrifuge 18. A platelet sensor is appropriately positioned in a portion of the platelet collect line 34 between the centrifuge 18 and the platelet collect bag 38. The platelet sensor generally includes a central detector, which coincides with the axis in which the light is initially directed through the flow, and annular detectors. These independent detectors are utilized in conjunction with each other to determine the instantaneous concentration of collected platelets passing by the monitoring device. Using this estimated platelet concentration and the flow rate of the platelets being collected and passing through the platelet collect line 34, the instantaneous rate at which platelets are being collected may be determined. By integration the current platelet yield may thus be determined. At the end of the given platelet harvesting procedure, this determination will thus constitute a monitored yield value.

Although the CCM provides valuable information, in order to enhance the accuracy of this monitored yield value, a calibration factor is applied to the platelet concentration prior to the described integration. This calibration factor is associated with the CCM (i.e., a predetermined yield monitoring technique) in relation to the predetermined off-line yield determination technique (i.e., laboratory testing regime such as the platelet counting device and/or platelet counting protocol).

The foregoing discussion of the yield determination aspect for use in combination with the harvesting aspect to provide the present invention was directed to one manner in which the associated platelet yields were generally derived. As noted above, both the predicted yield value and the monitored yield values are adjusted based upon a calibration factor. Each calibration factor is based upon the associated predetermined yield prediction technique and the predetermined yield monitoring technique, respectively, in relation to a predetermined off-line yield determination technique. One embodiment of the manner in which the present invention is initially configured, including providing appropriate calibration factors for the predetermined yield prediction and yield monitoring techniques, is generally illustrated by the flow chart of FIG. 3.

Figure 3:
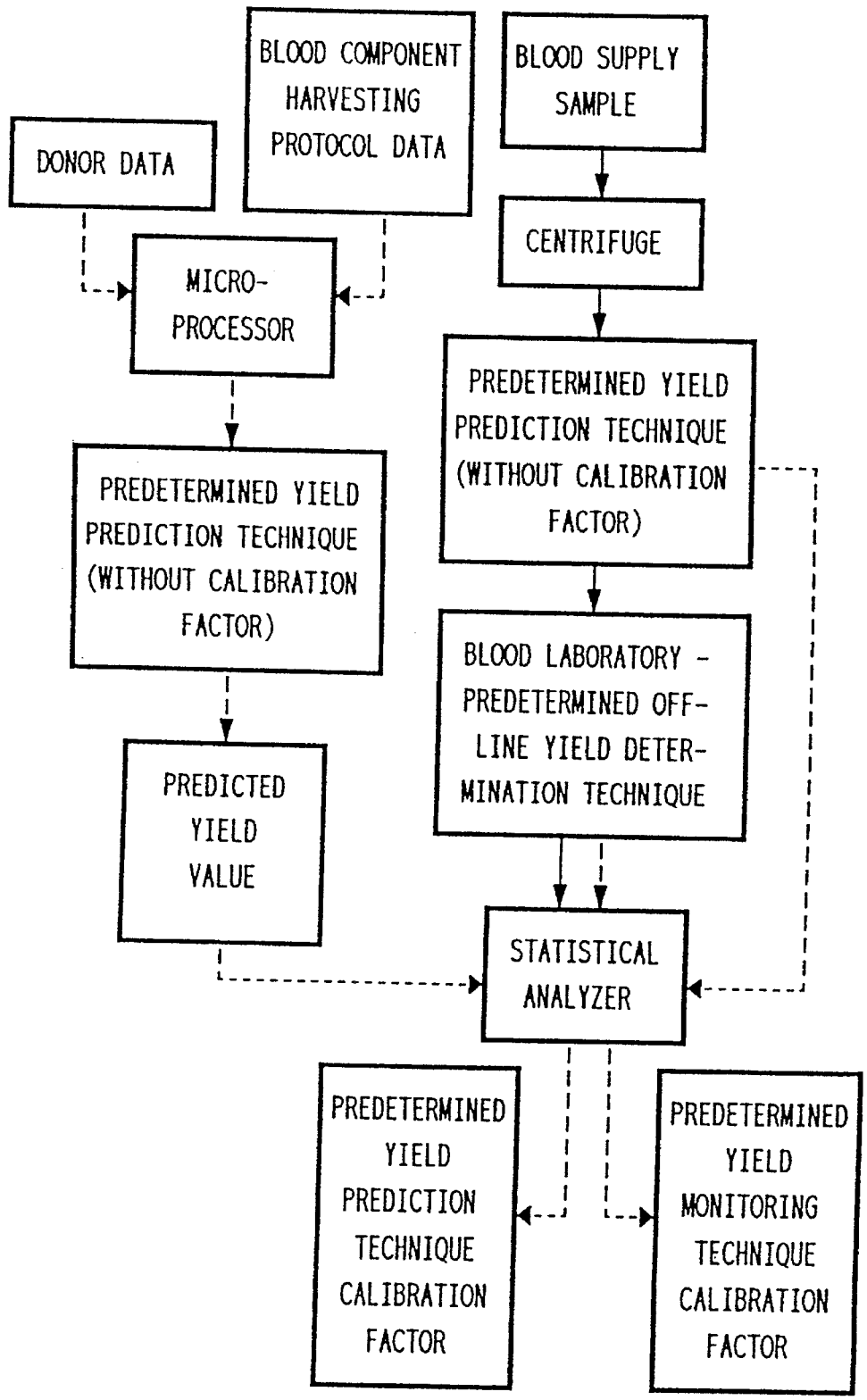
FIG. 3 is a schematic representation of one embodiment of a system for obtaining calibration factors for each of the predetermined yield prediction technique and predetermined yield monitoring technique.

Initially, in FIG. 3 the solid lines coincide with the transmission/provision of blood and/or blood components and the dashed lines coincide with the transmission/provision of information/data. Moreover, FIG. 3 illustrates the procedure which is preferably performed for a plurality of runs. Generally, the calibration factors for each such run are generated by computing a predicted yield value (e.g., using a predetermined yield prediction technique), monitored yield value (e.g., using a predetermined yield monitoring technique), and off-line measured yield value (e.g., using a predetermined off-line yield determination technique). Consequently, using the procedure of FIG. 3, a plurality of blood samples will individually undergo the procedure of FIG. 3, each such procedure producing a collection of harvested platelets (e.g., via blood component separation assembly 10 or 58).

With regard to the predetermined yield prediction technique and as illustrated in FIG. 3, appropriate donor and blood component harvesting protocol data associated with a first blood sample (e.g., a single run or procedure) are input into a microprocessor which utilizes the predetermined yield prediction technique without, however, its associated calibration factor. Consequently, a predicted yield value associated with the blood components harvested/to be harvested by the centrifuge is generated by the microprocessor.

During the harvesting of the blood components from the first blood sample by the centrifuge, the predetermined yield monitoring technique, without however its associated calibration factor, provides for a determination of the blood component concentration which is therefore utilized to obtain a monitored yield value for the platelets harvested from the first blood sample. More particularly, utilizing the flow rate of harvested blood components a microprocessor (not shown) is used to integrate the instantaneous flow rate to provide a monitored yield value. This monitored yield value is thus continually updated until completion of the procedure which thereby results in the final monitored yield value.

The harvested/collected blood components from the first blood sample are also subjected to a predetermined off-line yield determination technique to provide an off-line measured yield value. For instance, this may be accomplished by submitting the harvested/collected blood components to an appropriate laboratory for analysis of the same.

Based upon the three yield determinations for the particular blood sample, an appropriate calibration factor is provided for the predetermined yield prediction technique and the predetermined yield monitoring technique by, for instance, a statistical analyzer. More particularly the yield technique calibration factor for each run of a blood sample may be determined by dividing the associated off-line measured yield value by the predicted yield value. Similarly, the monitoring calibration factor may be determined by dividing the associated off-line measured yield value by the monitored yield value.

As can be appreciated, by utilizing an appropriate control group comprised of a plurality of runs of various blood samples to obtain the desired blood components, yield calibration factors of desired statistical significance may be determined by subjecting each such blood sample to the above procedure. This applies to initialization of the present invention to obtain system stability, as well as to a quality control feature in which the present invention may be periodically checked by further sampling (e.g., running one or more blood samples through the above-identified procedure) in accordance with the above to verify that the system continues to be stable, and such that the calibration factors continue to be of the desired statistical significance. In the event that such significance is no longer being achieved, the calibration factors may be appropriately updated and/or certain changes to the harvesting procedure may be desired/required.

Figure 4:
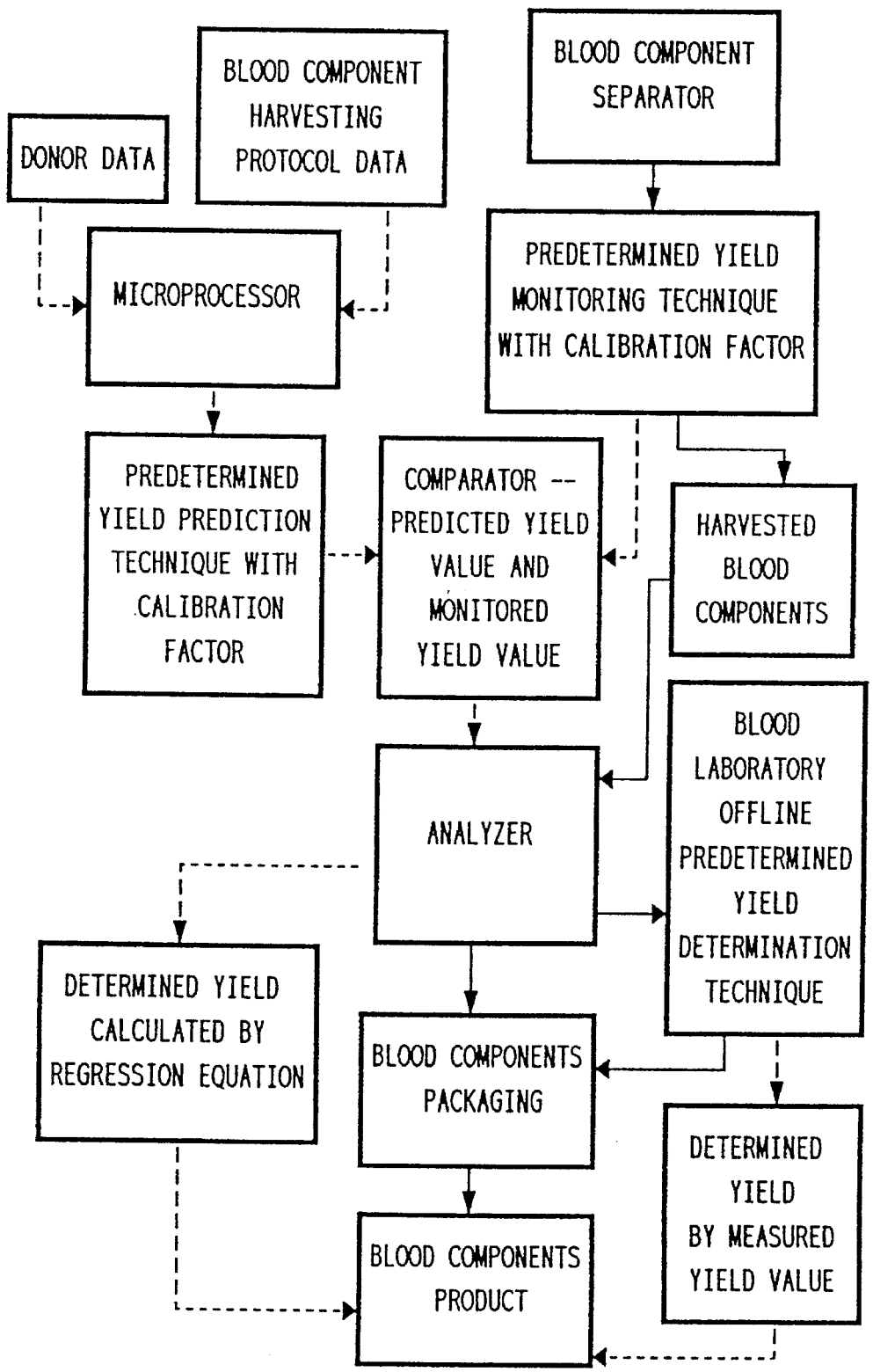
FIG. 4 is a schematic representation of one embodiment of a system in which blood component products are obtained in accordance with the present invention.

Once the desired calibration factors are obtained, the associated calibration factor may be provided to the predetermined yield prediction technique (e.g., by incorporation into Equation 1 above in the noted manner) and to the predetermined yield monitoring technique (e.g., by incorporating the yield calibration factor into the CCM prior to the described integration procedure). FIG. 4 illustrates a system 78 of one embodiment of the present invention which utilizes each of such calibration factors for purposes of providing a determined yield for association with a collection of harvested blood components. Consequently, this results in the provision of a blood component product. As in the case of FIG. 3, the solid lines of FIG. 4 continue to coincide with the transmission of blood and/or blood components, while the dashed lines coincide with the transmission/provision of information/data.

As illustrated in FIG. 4, a blood component separator (e.g., assembly 10 or 58, or portions thereof) is provided for the harvesting of blood components from whole blood in the above-described manner, such as by utilizing centrifugation or other appropriate blood component separation techniques. The harvested blood components flow through/by the system component incorporating the predetermined yield monitoring technique, utilizing its associated yield calibration factor, such that a monitored yield value is generated. Moreover, appropriate donor data and blood component harvesting protocol data is entered into the microprocessor such that the predetermined yield prediction technique, utilizing its associated yield calibration factor, will generate a predicted yield value.

When the predicted and monitored yield values are obtained for the run, they are compared to determine, for instance, if there is an agreement between the two yields which is within acceptable limits of probability. In the event that an acceptable comparison is determined, a regression equation is used to estimate the determined yield by the predicted and monitored yield values. For instance, a standard regression of the predicted yield value and the monitored yield value may be performed using a moving-average data base. The chosen form of the regression equation for the estimated yield may be any linear or non-linear relationship. Nonetheless, the comparison verifies that the generated data corresponds statistically to a normal run, and that no unusual events have occurred which may invalidate the yield estimate, or a standard statistical test (e.g., a normal test or a t test) may be used to determine whether the agreement between the two yields is within acceptable limits of probability. In the event that an unacceptable comparison is determined, the harvested blood components are provided to a laboratory for the performance of an off-line yield determination technique thereon to obtain an off-line measured yield value.

Once the yield is determined for a given collection of harvested blood components, such may be appropriately packaged. Moreover, the determined yield may then be associated therewith such that the desired blood component product is provided by the present invention.

For purposes of further illustrating the various features of the present invention, particularly those relating to the predetermined yield calibration technique, predetermined yield monitoring technique, and associated calibration factors, the following Examples are provided. Generally, the Examples pertain to platelet harvesting utilizing the COBE Spectra™ which is commercially available from Cobe BCT, Incorporated, supplemented to incorporate the present invention. Notwithstanding the presentation of such Examples, those skilled in the art will appreciate that the various details presented therein do not limit the scope of the present invention.

EXAMPLE 1

One embodiment of an appropriate predetermined yield prediction technique is presented herein with regard to the harvesting of platelets utilizing the blood component separation assembly 10 of FIG. 2. Initially, the predetermined yield prediction technique must be appropriately configured in conjunction with the blood component separation assembly 10 and the platelet harvesting protocol to be associated therewith. For instance, an anticoagulant infusion rate (e.g., the rate at which anticoagulant is provided to the whole blood from the AC container 30 prior to the whole blood entering the centrifuge 18) and the anticoagulant ratio must be specified. Moreover, in the event that plasma is to be collected into the plasma collect bag 54 in the procedure, the maximum amount of plasma which should be harvested considering the health of the donor 14 must also be provided. There are two alternatives for establishing this plasma volume limit.

The first alternative relating to the plasma volume limit is to provide a weight cutoff (e.g., 0–500 pounds), associated with the weight of the donor 14 which is input as will be discussed below. In this regard, a plasma volume upper limit (e.g., 10–1500 ml.) may be established for a weight of a donor 14 in excess of this cutoff, and a plasma volume lower limit (e.g., 10–1500 ml.) may be established for a weight of such donor 14 which is less than this cutoff. For instance, the weight cutoff may be established as 175 pounds, the plasma volume upper limit 600 ml. for a donor 14 weight greater than or equal to 175 pounds, and the plasma volume lower limit 500 ml. for a donor 14 weight less than 175 pounds.

The second alternative for a plasma volume limit is to configure the predetermined yield prediction technique such that the plasma volume limit is expressed a percentage of the total blood volume of the donor 14 which is calculated pursuant to Eq. 10 below. For instance, the plasma volume limit may be established as 1–15% of the total blood volume of the donor 14, and is preferably established as 12% of such volume.

Further information is required for configuration of the predetermined yield prediction technique. For instance, the procedure time is either input or arrived at based upon other criteria. However, the procedure time is typically 100 minutes. Moreover, a stepdown option may be utilized for the centrifuge 18 which may enhance separation of the various blood components. When this stepdown option is selected, the angular velocity of the centrifuge 18 is incrementally reduced during the platelet harvesting procedure. For instance, the stepdown option could provide for angular velocities for the centrifuge 18 of 2400, 2200, and 2000 RPM, each of which would be for a specified duration.

Based upon the foregoing, the configuration of the predetermined yield prediction technique in relation to the blood component separation assembly 10 and associated protocol in effect standardizes such for purposes of "normal" operations. However, for a particular donor 14 it may be desirable to only alter the "configuration" for the one processing run. Consequently, the present invention utilizes a procedure in which certain parameters utilized in the following equations may be adjusted on a one-time basis. Such is referred to as modified data input and the associated parameters are procedure time (e.g., 10–999 minutes), inlet flow rate for the centrifuge 18 (e.g., 0–150 ml/min. for the FIG. 1 assembly and 0–50 ml/min. for the FIG. 2 assembly), AC ratio option as discussed above, the desired platelet collect volume (e.g., 10–9999 ml.), the desired platelet collect concentration (e.g., 100–8000×10$^3$/ml.), and the desired source plasma volume to be collected (e.g., 0–9999 ml.).

Having configured the predetermined yield prediction technique in the above-described manner, the following additional information is provided and is utilized in the various calculations of Equations 1–23 presented below: (1) needle option, namely whether the procedure is dual needle (FIG. 1) or single needle (FIG. 2); (2) run identification number for purposes of associating the data/output generated by the various equations with a particular donor 14 and processing run; (3) the sex of the donor 14; (4) the height of the donor 14; (5) the weight of the donor 14; (6) the total blood volume as calculated in Eq. 10 below; (7) the hematocrit of the donor 14, either based upon an initial estimation and thereafter updated based upon analysis of the donor's 14 blood sample or input directly from such an analysis; (8) the platelet precount, either based upon an initial estimation and thereafter updated based upon analysis of the donor's 14 blood sample or input directly from such an analysis; and (9) whether plasma collection is desired in conjunction with the platelet collection.

Based upon the above initial configuration and subsequent data input, the following output is generated by the predetermined yield prediction technique: (1) platelet yield; (2) inlet flow rate; (3) AC ratio; (4) procedure time; (5) platelet collect volume; (6) platelet collect concentration; (7) source plasma volume; (8) AC in the platelet and plasma collect bags 38, 54; (9) platelet postcount; (10) AC infusion rate; and (11) output approval. All of this information is utilized at least in part in the following equations to generate, inter alia, the predicted platelet yield value of the collected platelets for the case of the dual needle procedure of FIG. 1. As will be appreciated, some of such equations are utilized in the calculation of the predicted platelet yield, whereas other of such equations are used to generate additional information for output and informational purposes. The various parameters and the units associated therewith of the equations are presented after the equations in the Variables Index and the equations are grouped in an appropriate manner.

Platelet Yield $$Y = 1 \times 10^6 \, C_{PR} \, V_B \, F_Y [1 - exp[-E_c \, (f_{BP} - 0.12)]] \quad \text{(Eq. 1)}$$

where:

$$f_{BP} = (Q_{IN} \, t_E + 50)(1 - 1/R)/V_B \quad \text{(Eq. 2)}$$

and where:

$$Q_{IN} = R Q_{AC} = 0.001 \, I \, V_B \, PR \leq 150 \quad \text{(Eq. 3)}$$

Alternatively, the platelet yield may be expressed as:

$$Y = 1 \times 10^6 C_{PR} V_B F_Y [1 - exp[-E_c(0.001 \, I(R-1)Pt_E + 50 \, (1-1/R)/V_B - 0.12]] \geq 0 \quad \text{(Eq. 4)}$$

Platelet Collection Efficiency $$E_c = C_1 - C_2 \, exp \, [9.91 \, (1-1/R)H] \, Q_{INA} \geq 0 \quad \text{(Eq. 5)}$$

where the constant $C_1$ is defined as follows:

$C_1 = 0.803$–dual needle, without stepdown $C_1 = 0.840$–dual needle, with stepdown where the constant $C_2$ is defined as follows:

$C_2 = 4.08 \times 10^{-5}$ – dual needle, without stepdown – dual needle, with stepdown and where:

$$Q_{INA} = Q_{IN} \, (t_E/t_P) \quad \text{(Eq. 6)}$$

In Eq. 6, $t_P$ may be provided as configuration data or modified data as provided above, or alternatively may be derived from the solution of Eq. 4 for $t_E$.

Effective Procedure Time $$t_E = t_p, Q_{IN} \leq 45 \quad \text{(Eq. 7)}$$
$$= t_p - 500(1/45 - 1/Q_{IN}), Q_{IN} > 45$$

Only high-flow protocol is used for $Q_{IN} > 45$.

AC Infusion Rate Constant $$I = 1000 \, Q_{IN}/(PRV_B) \quad \text{(Eq. 8)}$$

Alternatively to the use of Eq. 8 for the derivation of the AC infusion rate constant I, such may be provided as configuration or modified input data pursuant to the above.

AC Ratio

Initially, the AC ratio may be provided as configuration or modified input data pursuant to the above. In configuration, it is defined as follows:

$$R = 1 + 2.51/H \quad \text{low} \quad \text{(Eq. 9)}$$
$$= 1.33(1 + 2.51/H) \quad \text{medium}$$
$$= 1.67(1 + 2.51/H) \quad \text{high}$$

Total Blood Volume $$V_B = 604 + 0.006012 \, L^3 + 14.6 \, W \, \text{ml (male)} \quad \text{(Eq. 10)}$$
$$= 183 + 0.005835 \, L^3 + 15.0 \, W \, \text{ml (female)}$$

Plasma Collect Factor $$Q_{ACD} = 0.001 \, I \, V_B \quad \text{(Eq. 11)}$$

where:

$$Q_{INO} = RQ_{ACD} = 0.001 \, IRV_B \quad \text{(Eq. 12)}$$

where:

$$P = Q_{IN}/Q_{INO} = (\text{average } Q_{AC})/Q_{ACD} \quad \text{(Eq. 13)}$$

where:

$$P = 1 + (f_{ACP}/Q_{ACD})[V_C/(t_P - 150/Q_{IN}) + V_{SP}/(t_P - 500/Q_{IN})] \quad \text{(Eq. 14)}$$

and where:

$$f_{ACP} = [(R-1)(1-H)]^{-1} \quad \text{(Eq. 15)}$$

Platelet Collect Volume $$V_C = 1 \times 10^{-6} \, Y/[C_B(1+f_{ACP})] \quad \text{(Eq. 16)}$$

Source Plasma Volume

The four choices provided are as follows:

$$\left. \begin{array}{rcl} V_{SP} &=& 0 \\ &=& V_{CON} - V_C \\ &=& f_{SP} V_B - V_C \\ &=& \text{specified as modified input} \end{array} \right\} \geq 0 \quad \text{(Eq. 17)}$$

where:

$$V_{CON} = V_{CONL}, W < W_c \quad \text{(Eq. 18)}$$
$$= V_{CONH}, W \geq W_c$$

and where:

$$0.01 \leq f_{SP} \leq 0.15 \quad \text{(Eq. 19)}$$

Donor Postcount $$C_{PO} = C_{PR} \exp[-E_C(0.001 \, I(R-1)Pt_E + 50(1-1/R)/V_B - 0.12)] \leq C_{PR} \quad \text{(Eq. 20)}$$

A warning is given if $C_{PO} < 100$.

Collect Volumes $$V_{CB} = V_C (1 + f_{ACP}) \quad \text{(Eq. 21)}$$

$$V_{SPB} = V_{SP} (1 + f_{ACP}) \quad \text{(Eq. 22)}$$

where:

$$f_{ACB} = f_{ACP}/(1 + f_{ACP}) \quad \text{(Eq. 23)}$$

The primary equation to be solved for purposes of the present invention is Eq. 4 which provides the predicted platelet yield for use with the harvesting aspect to provide desired platelet products pursuant to the present invention. Consequently, Eqs. 1–3 and 5–23 are ancillary to Eq. 4 although they may be used to calculate other output data and/or information required by Eq. 4. As will be noted by a more detailed review of Eq. 4, such incorporates the above-discussed yield calibration factor which is again based upon the predetermined yield prediction technique and a predetermined off-line yield determination technique.

With regard to the manner in which Eqs. 1–23 are solved, all the iteration loops are based on the technique of successive approximation, in which each iteration is a repeat of the previous one, but using updated parameter values calculated in the previous iteration. This process continues until all the convergence criteria are met. The convergence criteria are that, on successive iterations, the variable difference is $\leq 1$ for $V_c$, $\leq 0.2$ for $t_E$, and $\leq 10$ for $C_B$.

As noted above, the foregoing was based upon a dual needle configuration as illustrated in FIG. 1. In the event that a single needle configuration such as that illustrated in FIG. 2 is utilized, the following Eq. 7' is used in place of Eq. 7 and the constants $C_1$ and $C_2$ for Eq. 5 are as follows:

$$c_1 = 0.803$$
$$c_2 = 8.54 \times 10 - 5$$

$$t_E = t_p, Q_{IN} \leq 20 \quad \text{(Eq. 7')}$$
$$= t_p - 215(1/20 - 1/Q_{IN}), Q_{IN} > 20$$

Variables Index

Symbols for Equations:

| | | |
|---|---|---|
| $C_1, C_2$ | = | constants in platelet collection efficiency equations |
| $C_B$ | = | platelet concentration in collect bag, $10^3$ platelets/microliter |
| $C_{PO}$ | = | donor postcount, $10^3$ platelets/microliter |
| $C_{PR}$ | = | donor precount, $10^3$ platelets/microliter |
| $E_C$ | = | platelet collection efficiency |
| $f_{ACB}$ | = | AC expressed as a fraction of plasma plus AC volume |
| $f_{ACP}$ | = | AC expressed as a fraction of pure plasma volume |
| $f_{BP}$ | = | fraction of $V_B$ processed in platelet collection procedure |
| $f_{SP}$ | = | $V_{CON}$ expressed as a fraction of $V_B$ |
| $F_Y$ | = | yield calibration factor |
| H | | hematocrit of donor or patient |
| I | = | AC infusion rate constant |
| L | = | donor or patient height, inches |
| P | = | plasma collect factor |
| $Q_{AC}$ | = | AC flow, ml/min |
| $Q_{ACD}$ | = | AC flow infused into donor for platelet collection procedures, ml/min |
| $Q_{IN}$ | = | inlet flow, ml/min |
| $Q_{INA}$ | = | average inlet flow for platelet procedures, ml/min |
| $Q_{INO}$ | = | $RQ_{ACD}$ = inlet flow associated with $Q_{ACD}$, ml/min |
| R | = | AC ratio |
| $t_E$ | = | equivalent procedure time, min |
| $t_P$ | = | procedure time, min |
| $V_B$ | = | total blood volume of donor or patient, ml |
| $V_C$ | = | volume of pure plasma in platelet collect bag, ml |
| $V_{CB}$ | = | total volume in platelet collect bag, ml |
| $V_{CON}$ | = | volume constraint for total pure plasma collected, ml |
| $V_{CONH}$ | = | higher value of $V_{CON}$, ml |
| $V_{CONL}$ | = | lower value of $V_{CON}$, ml |
| $V_{SP}$ | = | volume of pure plasma in source plasma bag, ml |
| $V_{SPB}$ | = | total volume in source plasma bag, ml |
| W | = | donor or patient weight, lbs |
| $W_C$ | = | weight constraint associated with $V_{CON}$, lb |
| Y | = | platelet yield, number of platelets. |

EXAMPLE 2

Figure 5:
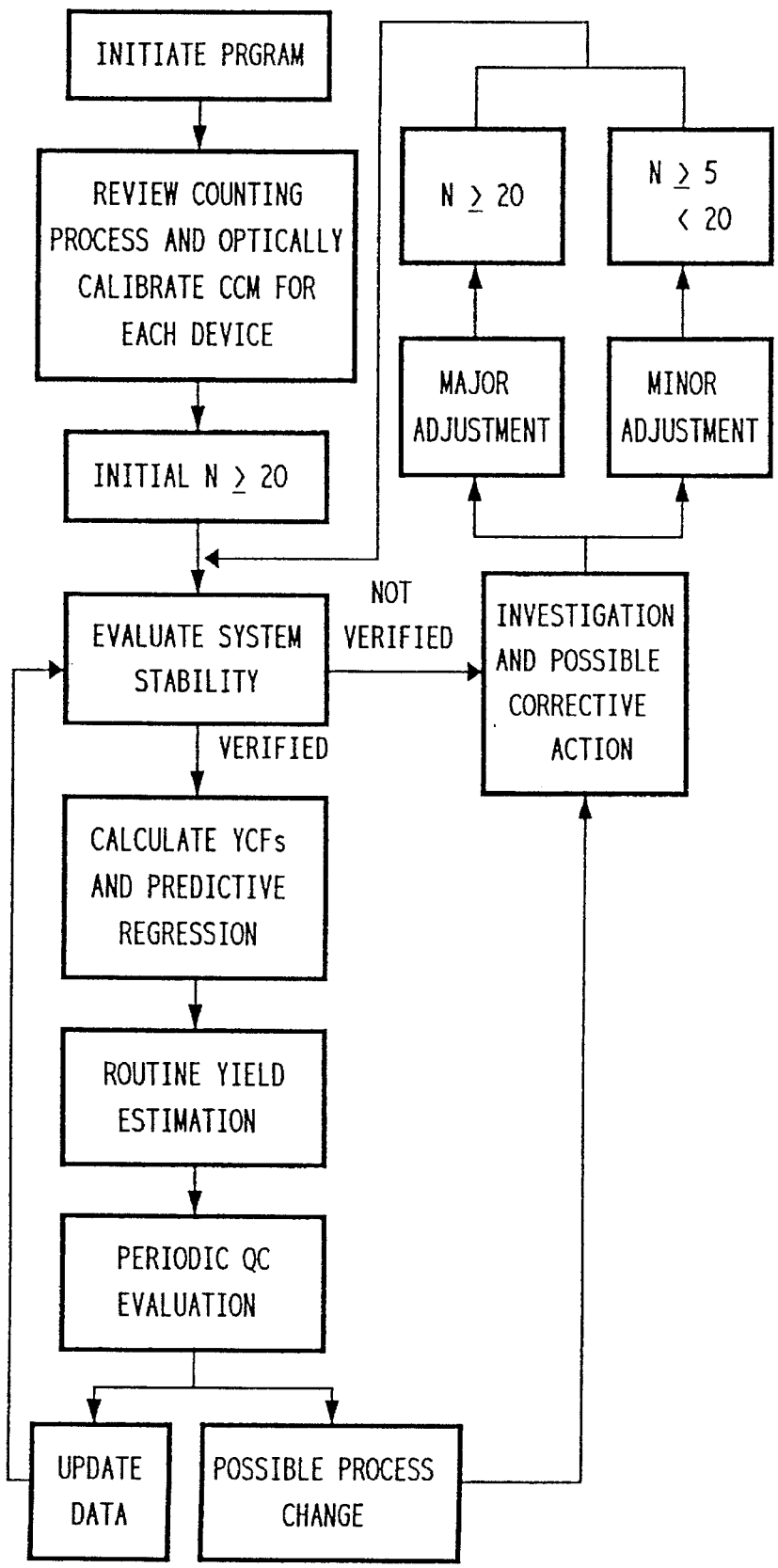
FIG. 5 is a schematic representation of one embodiment of a system for initializing the predetermined yield prediction technique, generating yield calibration factors for each of the predetermined yield prediction and predetermined yield monitoring techniques, and periodically evaluating such yield calibration factors.

One embodiment of the manner in which the calibration factors for both of the predetermined yield prediction technique of Example 1 above and predetermined yield monitoring technique of the above-identified CCM is more specifically addressed herein. Referring to FIG. 5, in order to determine that stability has been reached when processing a plurality of blood samples such that the predict and CCM yield calibration factors may be appropriately incorporated to obtain the predicted and CCM yield values, comparisons of the yields from the predetermined yield prediction technique and the CCM, each with the yield measurements from the predetermined off-line yield determination technique for a minimum of, for example, twenty runs are made. The particular algorithm used to determine stability is described in the following steps:

(a) At the initiation of a new set of process control parameters (e.g., configuration as described above), at least 20 consecutive runs are used to determine the parameter values. For each run, $Y_M$, $Y_P$ and $Y_C$ are determined. These runs constitute the initiation of a moving-average data base. During this procedure, limit-checking of all inputs for all consecutive runs in the sample is performed. If any one of the values is outside the limits, that run is excluded from the sample. More particularly, the procedure is as follows:

1. If the number of runs is less than 20, cancel data entry and stability determination ($N \leq 20$).
2. Verify that all yield values are within the following limits:

$$(1 < Y_M, Y_P, Y_C < 15 \ (\times 10^{11}))$$

If any one of the values is outside the limits, that run is excluded from the sample. The symbols are:
$Y_M$=measured yield from the predetermined off-line yield determination technique
$Y_P$=predict yield value from the predetermined yield prediction technique
$Y_C$=CCM yield value
N=number of runs in this sample (b) Calculate the ratios (YCFs) $X_i$ of individual predict yield value and CCM yield value with respect to the measured yield value.

$$X_{iP} = Y_M / Y_P$$

$$X_{iC} = Y_M / Y_C$$

(c) Eliminate outliers (for p=5%).
1. Calculate the means ($X_{mP}$ and $X_{mC}$) and the standard deviations ($S'_P$ and $S'_C$) of the N yield ratios. The means of these ratios represent the yield calibration factors for the predetermined yield prediction technique and CCM. Apply any one of the statistical outlier tests as described in the open literature, and eliminate the outliers from the sample. More particularly:
2. If either of the following occurs for a run $|X_{iP} - X_{mP}|_{MAX}/S'_P > 2.058 \ N^{0.1014}$ (for predetermined yield prediction technique) $|X_{iC} - X_{mC}|_{MAX}/S'_C > 2.058 \ N^{0.1014}$ (for CCM), then that run is classified as an outlier, and is excluded from the sample. The symbols are:
$X_i$=YCF for an individual run
$X_m$=mean value of N $X_i$s
S'=standard deviation of N $X_i$s
P,C=subscripts for predict and CCM, respectively
3. Remove the run from the sample, and decrement the number of runs by one.

$$N = N - 1$$

4. If the number of runs remaining in the sample N is less than 20, cancel the stability analysis until additional run data are available.
5. Continue the process of identifying outliers in steps 1 through 4, until all outliers have been removed.

(d) Divide N into subgroups of 5 runs each.
(e) Verify system stability which involves a comparison of the data from subgroups. System stability is not verified if any of the following (for example) occurs:
1. $|X_{mP} - 1| > 0.35$ (a specified maximum for predict).
2. $|X_{mC} - 1| > 0.35$ (a specified maximum for CCM).
3. $CV_P = S_P / X_{mP} > 0.20$ (a specified maximum for predict).
4. $CV_C = S_C / X_{mC} > 0.25$ (a specified maximum for CCM).
5. $|\bar{X}_P - X_{mP}| 3(S_P / N_s^{1/2} C_2)$ for any 1 sample.

19

6. $|\overline{X}_C - X_{mC}| 3(S_C/N_s^{1/2}C_2)$ for any 1 sample.
7. $|\overline{X}_P - X_{mP}| 2(S_P/N_s^{1/2}C_2)$ for 2 of any 3 consecutive samples.
8. $|\overline{X}_C - X_{mC}| 2(S_C/N_s^{1/2}C_2)$ for 2 of any 3 consecutive samples.

The symbols are:
CV=coefficient of variation
S=average of subgroup standard deviations
$\overline{X}$=average of subgroup $X_i$s
$N_s$=number of runs in each subgroup sample
$C_2$=statistical process control chart constant=0.8407 for $N_s$=5

(f) If stability is not verified, display status and the recommended corrective action. Recommended actions may include review of procedures, recalibration of instruments, and repair of the components involved.

(g) If stability is verified, procedures may be performed upon implementation of the yield calibration factors.

EXAMPLE 3

Figure 6:
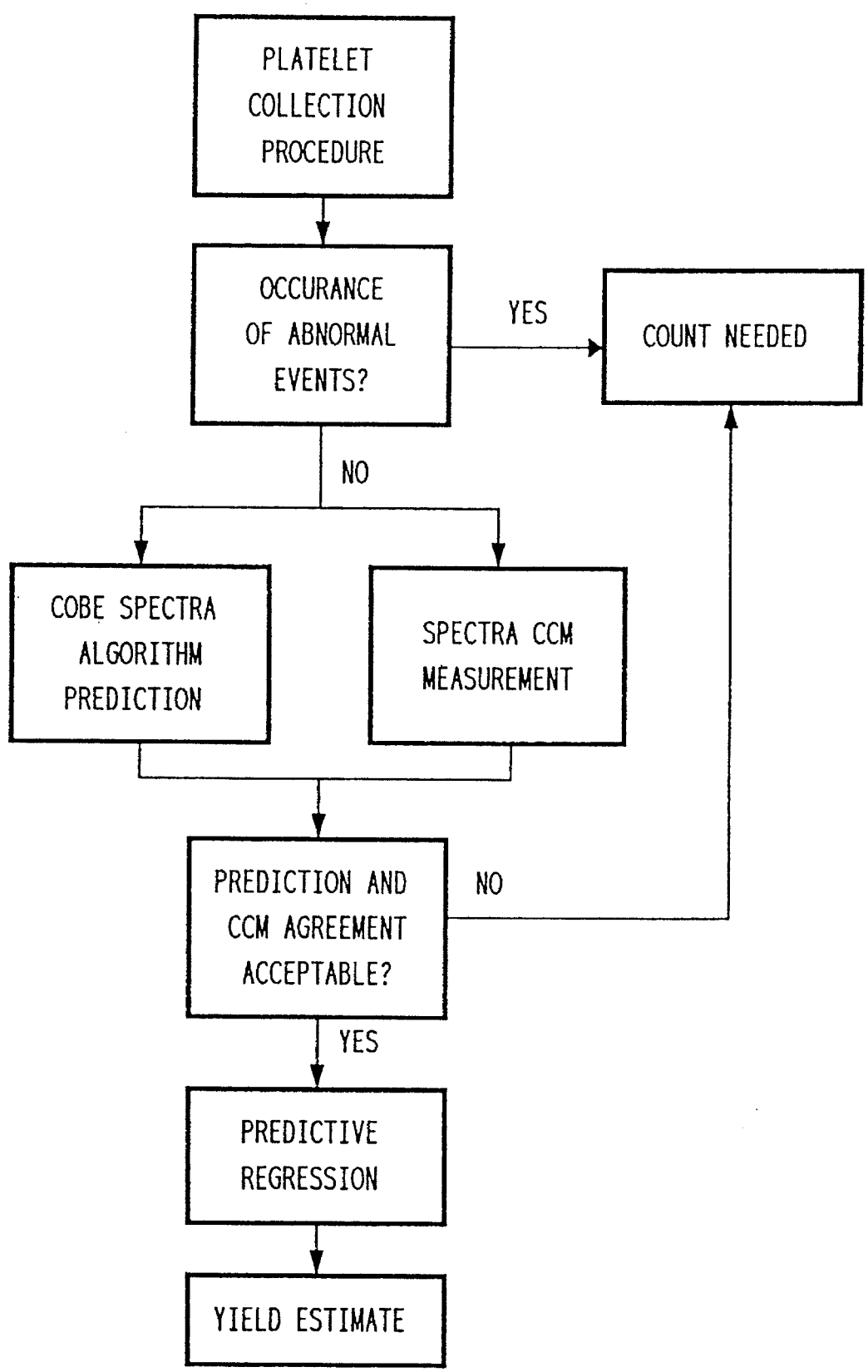
FIG. 6 is a schematic representation of one embodiment of the predetermined yield prediction technique in operation.

One embodiment of the manner in which a comparison is made between a predicted yield value and monitored yield value, for purposes of determining suitability of the agreement of such values, is presented herein and is illustrated in FIG. 6.

Perform a calculation utilizing the following equation:

$$1.960 - |X_{mP}(Y_P) - X_{mC}(Y_C)|/(S'^2_P + S'^2_C)^{1/2} < 0,$$

where the variables are as defined in Example 2 above. In the event that the test fails, the yield should be determined in accordance with a predetermined off-line yield determination technique.

EXAMPLE 4

Figure 7:
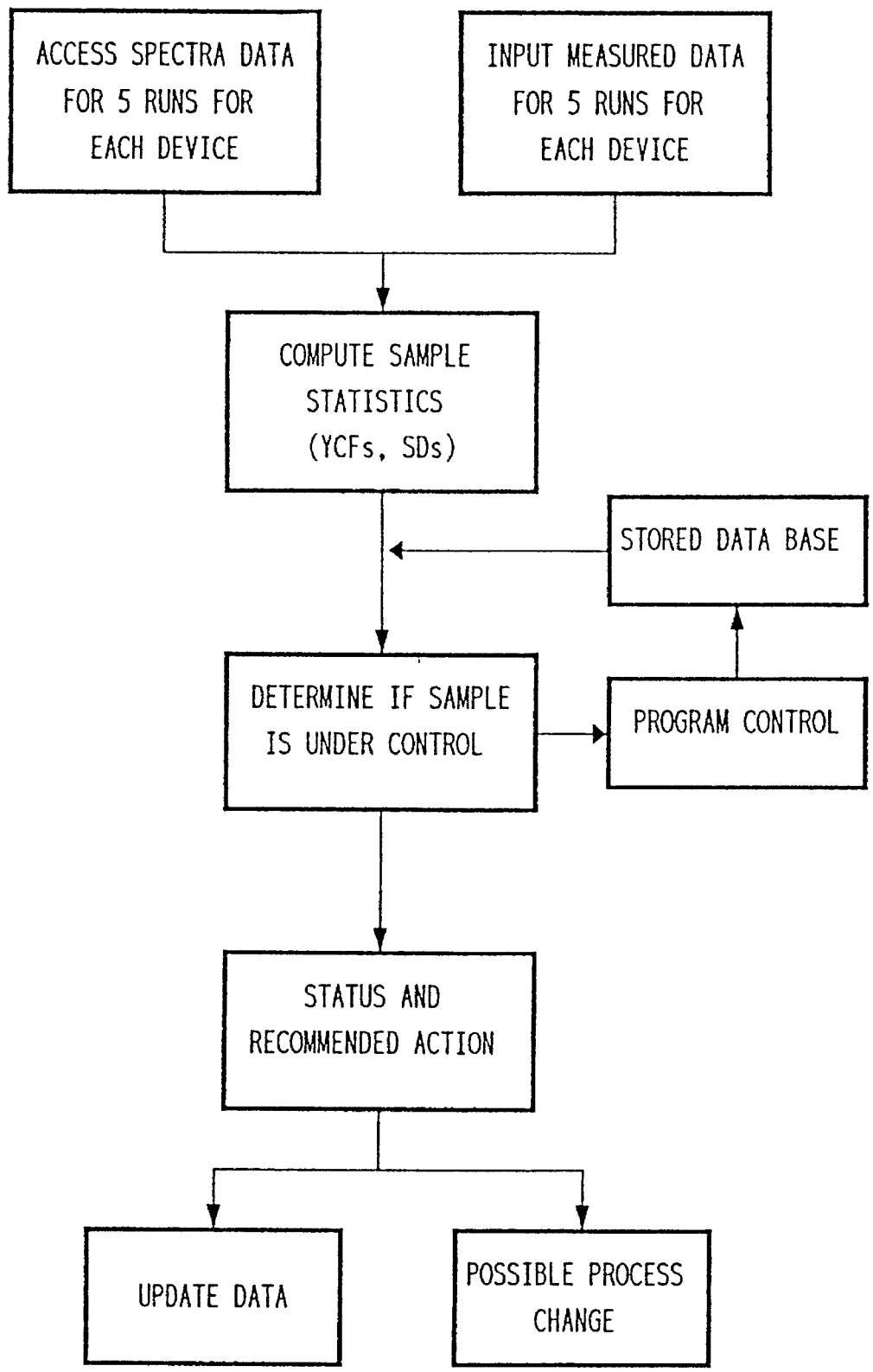
FIG. 7 is a schematic representation of a system for periodically monitoring operation of the system to verify the suitability of the yield calibration factors.

One embodiment of a quality control program for the present invention is presented herein and as illustrated in FIGS. 5 and 7. The quality control program is generally a periodic evaluation of the suitability of the yield calibration factors.

The algorithm to be used for the QC evaluation is as follows.

(a) Indicate to the operator when a QC evaluation is due to be performed.

(b) Analyze COBE Spectra™ yield data and laboratory-measured yields for five consecutive runs.

(c) Compute the mean ($\overline{X}$) and the standard deviation $S_s$ of the sample.

(d) Determine if the current sample is under control. It is not under control if any of the following (for example) occurs:
1. $|X_{iP} - \overline{X}_P|_{MAX}/S_{SP} > 2.058 \, N_s^{0.1014}$ (outlier criteria).
2. $|X_{iC} - \overline{X}_C|_{MAX}/S_{SC} > 2.058 \, N_s^{0.1014}$ (outlier criteria).
3. $|\overline{X}_P - X_{mP}| > 3(S_P/N_s^{1/2}C_2)$
4. $|\overline{X}_C - X_{mC}| > 3(S_C/N_s^{1/2}C_2)$
5. $|\overline{X}_P - X_{mP}| > 2(S_P/N_s^{1/2}C_2)$ for any 2 of the last 3 samples, including the current one.
6. $|\overline{X}_C - X_{mC}| > 2(S_C/N_s^{1/2}C_2)$ for any 2 of the last 3 samples, including the current one.
7. $\overline{X}_P - X_{mP}$ for the last 9 samples, including the current one, are not all positive or all negative.
8. $\overline{X}_C - X_{mC}$ for the last 9 samples, including the current one, are not all positive or all negative.

20

The symbols are:
$X_{iP}$=predict YCF for a run in the current sample.
$X_{iC}$=CCM YCF for a run in the current sample.
$\overline{X}_P$=mean of $X_{iP}$.
$\overline{X}_C$=mean of $X_{iC}$.
$X_{mP}$=mean predict YCF for current moving average.
$X_{mC}$=mean CCM YCF for current moving average.
$S_{SP}$=standard deviation of $X_{iP}$.
$S_{SC}$=standard deviation of $X_{iC}$.
$S_P$=average subgroup predict standard deviation for current moving average.
$S_C$=Average subgroup CCM standard deviation for current moving average.

(e) If the sample is not under control, display recommended action. Recommended actions may include review of procedures, recalibration of instruments, and repair of the components involved.

(f) If the sample is under control:
1. Incorporate sample into data base and into moving average.
2. Recalculate YCF($X_m$), S, and the regression equation constants.
3. Control a time-sequenced data base for the predict algorithm and the CCM for each machine. The data base consists of a number of runs, dated, identified, numbered, and with the following minimum information for each run: (1) measured yield, (2) predict yield, and (3) CCM yield. In addition, other relevant information should be stored for each run; e.g., the outcome of statistical analyses and control tests, whether an unusual event occurred, or whether the donor is unusual and not part of the normal donor/system performance distribution.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention, and such other embodiments, and with various modifications required by the particular applications or uses of the present invention. It is intended that the appended claims be construed to include alternative embodiments to the extent permitted by the prior art.

What is claimed is:

1. A system for providing a blood component product, comprising:

a blood component collection device;

a blood component yield predictor associated with said blood component collection device, wherein said blood component yield predictor provides on-line blood component yield determination capabilities; and means for calibrating said blood component yield predictor to a blood component yield counter, said blood component yield counter providing off-line blood component yield determination capabilities, wherein a predicted yield value, generated by said blood component yield predictor from a blood component collection procedure in which a blood component collection is provided by said blood component collection device, is adjusted to an adjusted predicted yield value, and wherein a blood component yield associated with said blood component collection to define a blood component product is based on said adjusted predicted yield value.

2. A system, as claimed in claim 1, wherein:

said blood component collection device comprises a centrifuge.

3. A system, as claimed in claim 1, wherein:

said blood component yield predictor comprises a processor, a primary yield prediction algorithm which generates said adjusted predicted yield value, and a plurality of ancillary yield prediction algorithms which provide information used by said primary yield prediction algorithm.

4. A system, as claimed in claim 1, wherein:

said means for calibrating said blood component yield predictor comprises means for repeating a calibration procedure for each of a plurality of calibrating blood sources, said calibration procedure comprising:

means for performing a blood component collection procedure using said blood component collection device to obtain a calibrating blood component collection from one of said calibrating blood sources;

means for predicting a yield of said calibrating blood component collection, said means for predicting using said blood component yield predictor and generating a calibrating predicted yield value;

means for counting a yield of said calibrating blood component collection, said means for counting using a blood component yield counter and generating a calibrating counted yield value, said blood component yield counter providing off-line blood component yield determination capabilities;

means for comparing said calibrating predicted yield value and said calibrating counted yield value, said means for comparing providing a calibrating differential; and means for deriving a calibration factor for use by said means for calibrating said blood component yield predictor from each said calibrating differential from each of said calibration procedures.

5. A system, as claimed in claim 1, further comprising:

a blood component yield monitoring device associated with said blood component collection device, wherein said blood component yield monitoring device provides on-line blood component yield determination capabilities; and means for calibrating said blood component yield monitoring device to a blood component yield counter, said blood component yield counter providing off-line blood component yield determination capabilities, wherein a monitored yield value, generated by said blood component yield monitoring device from said blood component collection procedure in which said blood component collection is provided by said blood component collection device, is adjusted to an adjusted monitored yield value, wherein said blood component yield associated with said blood component collection to define said blood component product is based on said adjusted monitored yield value in addition to said adjusted predicted yield value.

6. A system, as claimed in claim 5, wherein:

said means for calibrating said blood component yield monitoring device comprises means for repeating a calibration procedure for each of a plurality of calibrating blood sources, said calibration procedure comprising:

means for performing a blood component collection procedure using said blood component collection device to obtain a calibrating blood component collection from one of said calibrating blood sources;

means for monitoring a yield of said calibrating blood component collection, said means for monitoring using said blood component yield monitoring device and generating a calibrating monitored yield value;

means for counting a yield of said calibrating blood component collection, said means for counting using a blood component yield counter and generating a calibrating counted yield value, said blood component yield counter providing off-line blood component yield determination capabilities;

means for comparing said calibrating monitored yield value and said calibrating counted yield value, said means for comparing providing a calibrating differential; and means for deriving a calibration factor for use by said means for calibrating said blood component yield monitoring device from each said calibrating differential from each of said calibration procedures.

7. A system, as claimed in claim 1, further comprising:

means for packaging said blood component collection; and labeling on said means for packaging for said blood component collection, said labeling including said blood component yield.

8. A system for providing a blood component product having a determined yield pursuant to at least one on-line yield determination technique, comprising:

means for harvesting a plurality of a predetermined type of a blood component from a source of blood which is fluidly interconnected with said means for harvesting to form harvested blood first means for providing a first set of predetermined information relating to said source of blood, said source blood being from a living donor and said first set of predetermined information comprising at least one of said donor's hematocrit, height, weight and total blood volume;

second means for providing a second set of predetermined information relating to said means for harvesting, said second set of predetermined information comprising at least one of a collection efficiency for obtaining said harvested blood components, a number of fluid interconnections between said donor and said means for harvesting, at least one flow rate associated with said means for harvesting, and a duration in which said means for harvesting will be used for obtaining said harvested blood components;

third means for generating a predicted yield value of said harvested blood components based upon said first and second sets of predetermined information, said third means comprising a first at least one on-line yield determination technique, said predicted yield value being used for determination of said determined yield of said blood component product;

fourth means for providing a first calibration factor for calibrating said third means in relation to a predetermined off-line yield determination technique, said predetermined off-line yield determination technique allowing for determining an off-line measured yield value of said harvested blood components;

fifth means for generating said determined yield, said fifth means utilizing an application of said first calibration factor to said predicted yield value; and sixth means for packaging said harvested blood components and associating said determined yield therewith to provide said blood component product.

9. A system, as claimed in claim 8, further comprising:

seventh means for providing a monitored yield value of said harvested blood components, said seventh means comprising means for monitoring said harvested blood components, said seventh means comprising a second at least one on-line yield determination technique; and eighth means for providing a second calibration factor for calibrating said seventh means in relation to said predetermined off-line yield determination technique, wherein said fifth means utilizes an application of said second calibration factor to said monitored yield value to obtain said determined yield in addition to an application of said calibration factor to said predicted yield value.

10. An assembly for providing a blood component product having a determined yield pursuant to at least two on-line yield determination techniques, comprising:

means for harvesting a plurality of a desired blood component from a source of blood which is fluidly interconnected with said means for harvesting to form harvested blood components;

means for providing a first set of predetermined information relating to said source of blood, said source of blood being from a living donor and said first set of predetermined information comprising at least one of said donor's hematocrit, height, weight and total blood volume;

means for providing a second set of predetermined information relating to said means for harvesting, said second set of predetermined information comprising at least one of a collection efficiency for obtaining said harvested blood components, a number of fluid interconnections between said donor and said means for harvesting, at least one flow rate associated with said means for harvesting, and a duration in which said means for harvesting will be used for obtaining said harvested blood components;

means for predicting a first predicted yield value for said harvested blood components based upon said first and second sets of predetermined information, said means for predicting comprising a first of said at least two on-line yield determination techniques;

means for monitoring said harvested blood components to obtain a first monitored yield value for said harvested blood components, said means for monitoring comprising a second said at least two on-line yield determination techniques;

means for applying a first calibration factor, which calibrate; said means for predicting in relation to a predetermined off-line yield determination technique, to said first predicted yield value to obtain a second predicted yield value;

means for applying a second calibration factor, which calibrates said means for monitoring in relation to said predetermined off-line yield determination technique, to said first monitored yield value to obtain a second monitored yield value;

means for deriving said determined yield from said second predicted yield value and said second monitored yield value; and means for packaging said harvested blood components, whereby said determined yield value is identified with said packaged blood components to provide said blood component product.

* * * * *